United States Patent [19]

Sakamoto et al.

[11] Patent Number: 5,116,875

[45] Date of Patent: May 26, 1992

[54] BENZOYLUREA DERIVATIVE AND ITS PRODUCTION AND USE

[75] Inventors: Noriyasu Sakamoto; Tatsuya Mori, both of Takarazuka; Tadashi Ohsumi, Nishinomiya; Hiroaki Fujimoto, Takarazuka; Izumi Fujimoto, Minoo, all of Japan

[73] Assignee: Sumitomo Chemical Company, Limited, Osaka, Japan

[21] Appl. No.: 560,231

[22] Filed: Jul. 25, 1990

Related U.S. Application Data

[63] Continuation of Ser. No. 171,900, Mar. 22, 1988, abandoned.

[30] Foreign Application Priority Data

Apr. 3, 1987 [JP] Japan .................. 62-83513
May 6, 1987 [JP] Japan .................. 62-111489
Aug. 5, 1987 [JP] Japan .................. 62-196745

[51] Int. Cl.$^5$ .................. A01N 47/34; C07C 275/54
[52] U.S. Cl. .................. 514/594; 514/584; 564/23; 564/44; 564/24
[58] Field of Search .................. 564/23, 24, 430, 44; 514/594, 584

[56] References Cited

U.S. PATENT DOCUMENTS

| | | | |
|---|---|---|---|
| 4,005,223 | 1/1977 | Sirrenberg et al. | 424/322 |
| 4,275,077 | 6/1981 | Becher et al. | 424/322 |
| 4,331,817 | 5/1982 | Throckmorton | 564/430 |
| 4,399,152 | 8/1983 | Brouwer et al. | 424/322 |
| 4,529,819 | 8/1985 | Clifford et al. | 564/44 |
| 4,698,365 | 10/1987 | Anderson | 564/40 X |
| 4,774,260 | 9/1980 | Sirrenberg et al. | 564/23 X |

FOREIGN PATENT DOCUMENTS

| | | |
|---|---|---|
| 40924 | 7/1985 | Australia . |
| 0013414 | 12/1979 | European Pat. Off. . |
| 2537413 | 3/1977 | Fed. Rep. of Germany . |
| 1460410 | 8/1974 | United Kingdom . |
| 1488644 | 7/1975 | United Kingdom . |
| 8603941 | 7/1986 | World Int. Prop. O. . |

*Primary Examiner*—Glennon H. Hollrah
*Assistant Examiner*—B. M. Burn
*Attorney, Agent, or Firm*—Stevens, Davis, Miller & Mosher

[57] ABSTRACT

A novel benzxoylurea derivative represented by the formula (I) described below, its production and an insecticidal and/or acaricidal composition containing it as an active ingredient:

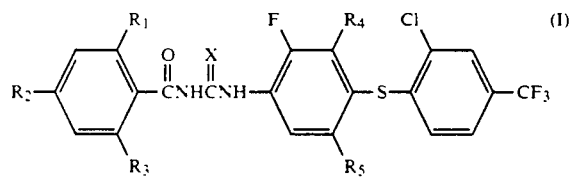

wherein $R_1$ is a chlorine or fluorine atom, each of $R_2$ and $R_3$, wherein may be the same or different, is a fluorine or hydrogen atom, $R_4$ is a chlorine or hydrogen atom, $R_5$ is a halogen atom or a methyl or trifluoromethyl group, and X is an oxygen or sulfur atom.

16 Claims, No Drawings

BENZOYLUREA DERIVATIVE AND ITS PRODUCTION AND USE

This application is a continuation of application Ser. No. 07/171,900, filed Mar. 22, 1988, now abandoned.

The present invention relates to a novel benzoylurea derivative represented by the formula (I) described below, its production and an insecticidal and acaricidal composition containing it as an active ingredient:

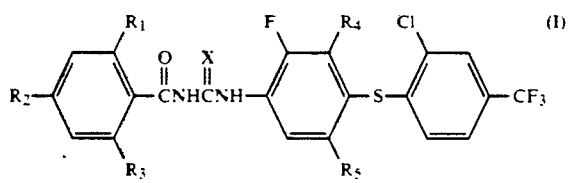

wherein $R_1$ is a chlorine or fluorine atom, each of $R_2$ and $R_3$, which may be the same or different, is a fluorine or hydrogen atom, $R_4$ is a chlorine or hydrogen atom, $R_5$ is a halogen atom or a methyl or trifluoromethyl group, and X is an oxygen or sulfur atom.

The present inventors have extensively studied to develop a benzoylurea compound having excellent insecticidal and acaricidal activity, and as a result, have found that the benzoylurea derivative represented by the formula (I) (hereinafter referred to as present compound) has a very high insecticidal and acaricidal activity, particularly a high lethal activity against the larvae and nymphs of spider mites and a sterilization activity against the female adults of spider mites as well as an ovicidal activity, and also that it can be produced at a relatively low cost. The present inventors thus attained the present invention.

Among the present compounds represented by the formula (I), preferred ones include those in which $R_1$ is a chlorine or fluorine atom, $R_2$ is a hydrogen atom, $R_3$ is a hydrogen atom when $R_1$ is a chlorine atom, and a fluorine atom when $R_1$ is a fluorine atom, $R_4$ is a hydrogen atom, $R_5$ is a halogen atom or a methyl or trifluoromethyl group, and X is an oxygen atom.

U.S. Pat. No. 3,933,908 discloses benzoylurea compounds which are efficacious against insect pests, and among these compounds, diflubenzuron is already on the market. Also, it is known that compounds disclosed in EP-A1-161019 have not only an insecticidal activity, but also an acaricidal activity.

Although these compounds exhibit an insecticidal activity against insect pests belonging to Lepidoptera, etc., their acaricidal activity is so poor that they are not always satisfactory as an acaricide. Contrary to this, it has been found that the present compounds have excellent insecticidal and acaricidal activity.

For specific examples of insect pests against which the present compounds are particularly efficacious, there may be given the following insects and mites: Larvae of Lepidoptera such as diamond-back moth (*Plutella xylostella*), rice stem borer (*Chilo suppressalis*), rice leafroller (*Cnaphalocrocis medinalis*), armyworms and cutworms, etc.; larvae of Diptera such as house mosquitoes (Culex spp.) [e.g. common mosquito (*Culex pipiens pallens*)], Anopheline mosquitoes (Anopheles spp.), Aedes mosquitoes (Aedes spp.), chironomid midges (Chironomidae), houseflies (Muscidae) [e.g. *Musca domestica*], blow flies (Calliphoridae), flesh flies (Sarcophagidae), tabanid flies (Tabanidae), blackflies (Simulidae), etc.; nymphs of Dictyoptera [e.g. German cockroach (*Blattella germanica*)]; larvae of Coleoptera; and spider mites (Tetranychidae) such as two-spotted spider mite (*Tetranychus urticae*), carmine spider mite (*Tetranychus cinnabarinus*), Kanzawa spider mite (*Tetranychus kanzawai*), citrus red mite (*Panonychus citri*), European red mite (*Panonychus ulmi*), etc.; cheyletid mites (Cheyletidae); tarsonemid mites (Tarsonemidae); acarid mites (Acaridae) [e.g. mold mite (*Tyrophagus putrescentiae*)]; pyroglyphid mites (Pyroglyphidae) [e.g. Dermatophagoides farinae]; etc.

Also, the present compounds are low in toxicity to warm-blooded animals so that it can be orally administered mixed with feeds for animals to domestic animals such as cattle, pigs, horses, sheep, goats, chickens, etc. As a result, the present compounds are excreted from animals as undecomposed, so that the larvae of insects living in the excrements of domestic animals [e.g. housefly, false stablefly (*Muscina stabulans*), little housefly (*Fannia canicularis*), blow flies (Calliphoridae), flesh flies (Sarcophagidae), sepsid flies (Sepsidae)], can be exterminated.

For example, the following compounds may be given as the present compound:

N-(2,6-difluorobenzoyl)-N'-[2,5-difluoro-4-{2-chloro-4-(trifluoromethyl)phenylthio}phenyl]urea N-(2-chlorobenzoyl)-N'-[2,5-difluoro-4-{2-chloro-4-(trifluoromethyl)phenylthio}phenyl]urea N-(2,4,6-trifluorobenzoyl)-N'-[2,5-difluoro-4-{2-chloro-4-(trifluoromethyl)phenylthio}phenyl]urea N-(2,6-difluorobenzoyl)-N'-[2,5-difluoro-4-{2-chloro-4-(trifluoromethyl)phenylthio}phenyl]thiourea N-(2,6-difluorobenzoyl)-N'-[3-chloro-2,5-difluoro-4-{2-chloro-4-(trifluoromethyl)phenylthio}phenyl]urea N-(2,6-difluorobenzoyl)-N'-3,5-dichloro-2-fluoro-4-{2-chloro-4-(trifluoromethyl)phenylthio}phenyl]urea N-(2,6-difluorobenzoyl)-N'-[5-bromo-2-fluoro-4-{2-chloro-4-(trifluoromethyl)phenylthio}phenyl]urea N-(2,6-difluorobenzoyl)-N'-[2-fluoro-5-trifluoromethyl-4-{2-chloro-4-(trifluoromethyl)-phenylthio}phenyl]urea N-(2,6-difluorobenzoyl)-N'-[5-bromo-3-chloro-2-fluoro-4-{2-chloro-4-(trifluoromethyl) phenylthio}-phenyl]urea N-(2,6-difluorobenzoyl)-N'-[3-chloro-2-fluoro-5-trifluoromethyl-4-{2-chloro-4-(trifluoromethyl)-phenylthio}phenyl]urea N-(2,6-difluorobenzoyl)-N'-[5-chloro-2-fluoro-4-{2-chloro-4-(trifluoromethyl)phenylthio}phenyl]urea N-(2,6-difluorobenzoyl)-N'-[2-fluoro-5-methyl-4-{2-chloro-4-(trifluoromethyl)phenylthio}phenyl]urea N-(2-chlorobenzoyl)-N'-[5-chloro-2-fluoro-4-{2-chloro-4-(trifluoromethyl)phenylthio}phenyl]urea N-(2,4,6-trifluorobenzoyl)-N'-[5-chloro-2-fluoro-4-{2-chloro-4-(trifluoromethyl)phenylthio}phenyl]urea N-(2,6-difluorobenzoyl)-N'-[5-chloro-2-fluoro-4-{2-chloro-4-(trifluoromethyl)phenylthio}phenyl]thiourea The present compounds represented by the formula (I) can be produced by the following methods. Method A:

A method of reacting a benzoyl isocyanate compound or benzoyl isothiocyanate compound represented by the formula (II),

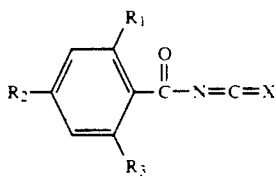

wherein $R_1$, $R_2$, $R_3$ and $X$ are the same as described above, with an aniline compound represented by the formula (III),

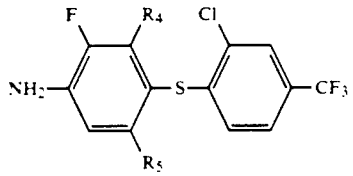

wherein $R_4$ and $R_5$ are the same as described above.

Method B:

A method of reacting a benzamide compound represented by the formula (IV),

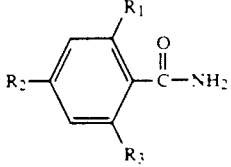

wherein $R_1$, $R_2$ and $R_3$ are the same as described above, with an isocyanate compound or isothiocyanate compound represented by the formula (V),

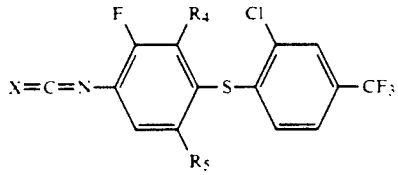

wherein $R_4$, $R_5$ and $X$ are the same as described above.

In the foregoing Methods A and B, the reaction is usually carried out in the presence of an inert solvent. The solvent usable includes for example aromatic hydrocarbons (e.g. benzene, toluene, xylene), halogenated hydrocarbons (e.g. chlorobenzene, carbon tetrachloride, chloroform, methylene chloride, 1,2-dichloroethane), ethers (e.g. diethyl ether, tetrahydrofuran, dioxane), ketones (e.g. acetone, methyl ethyl ketone, methyl isobutyl ketone), dimethyl sulfoxide, dimethylformamide, nitromethane and mixtures thereof.

In Methods A and B, the reaction can generally be carried out under normal pressure, and the reaction will be completed usually in from 1 to 50 hours. The amounts of the compounds which are a raw material are generally in an equimolar ratio, but one of the compounds may be used in excess.

In Methods A and B, the reaction temperature is not particularly limited, but it is in a range of generally from 0° to 80° C., usually from room temperature to 60° C. for Method A, and generally from room temperature to 160° C., usually from 80° to 130° C. for Method B.

The present compounds thus obtained can be purified if necessary by means such as column chromatography, recrystallization, etc.

Both the benzoyl isocyanate compound or benzoyl isothiocyanate compound represented by the formula (II) and the benzamide compound represented by the formula (IV), used in the methods of the present invention, are a known compound. The aniline compound represented by the formula (III) is a novel compound, and it can be produced, for example, by the following method:

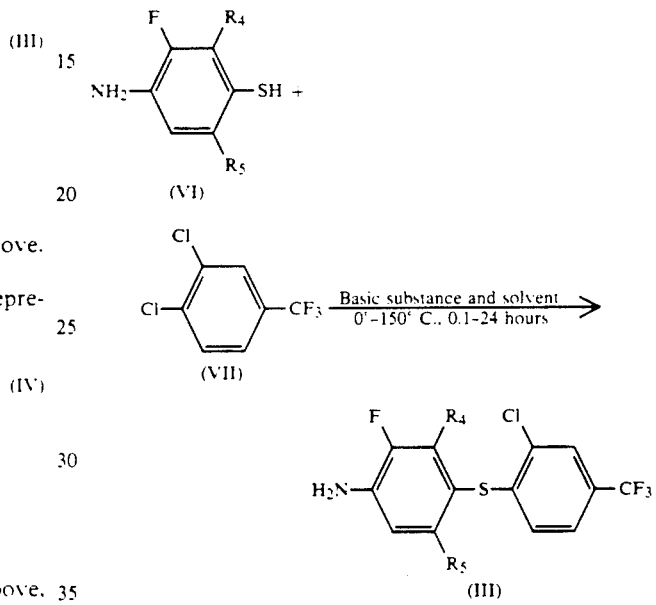

wherein $R_4$ and $R_5$ are the same as described above.

The basic substance used includes for example sodium hydroxide, potassium hydroxide, sodium carbonate, potassium carbonate, sodium hydride, potassium hydride, triethylamine, etc. The solvent used includes for example aprotic polar solvents such as dimethylformamide, dimethyl sulfoxide, hexamethylphosphoroamide, acetonitrile, etc.

In carrying out this reaction, the amount of the basic substance used is from about 0.5 to about 3 times by mole, preferably from about 1 to about 1.2 times by mole based on 1 mole of the aminothiophenol compound (VI), and the amount of the 3,4-dichlorobenzotrifluoride (VII) used is from about 0.5 to about 3 times by mole, preferably from about 1 to about 2 times by mole based on 1 mole of the same.

The reaction product thus obtained may be purified if necessary by means such as column chromatography, recrystallization, etc.

The aminothiophenol compound (VI) described in the foregoing reaction formula can be produced, for example, by the method disclosed in JP-A-60-181067, etc.

The isocyanate compound or isothiocyanate compound represented by the formula (V) can easily be produced by reacting an aniline compound represented by the formula (III) with phosgene or thiophosgene according to the usual method. This reaction is usually carried out under the following condition: The amount of phosgene or thiophosgene used is usually from 0.2 to 20 times based on the aniline compound, and an inert solvent is usually used. Normally, the solvent includes for example hydrocarbons (e.g. hexane, heptane, benzene, toluene), halogenated hydrocarbons (e.g. dichloromethane, chloroform, 1,2-dichloroethane, chlorobenzene) and mixtures of two or more of them. This reaction proceeds well in a range of from room temperature to the boiling point of the solvent. The reaction product thus obtained may easily be purified if necessary by distillation, etc.

When the present compounds are used as an active ingredient for insecticidal and acaricidal compositions, they may be used as they are without adding any other ingredients. Usually, however, they are formulated into emulsifiable concentrates, wettable powders, dusts, granules, flowable formulations, oil sprays, aerosols, poisonous baits, etc. by mixing with solid carriers, liquid carriers, gaseous carriers, surface active agents, other auxiliaries for formulation, baits, etc.

In these preparations, the content of the present compounds, which are an active ingredient, is from 0.01 to 95% by weight. The solid carrier includes for example fine powders or granules of kaolin clay, attapulgite clay, bentonite, terra abla, pyrophyllite, talc, diatomaceous earth, calcite, corn stalk powder, walnut shell powder, urea, ammonium sulfate, synthetic hydrated silicon dioxide and the like. The liquid carrier includes for example aliphatic hydrocarbons (e.g. kerosene), aromatic hydrocarbons (e.g. benzene, toluene, xylene, methylnaphthalene), halogenated hydrocarbons (e.g. dichloroethane, trichloroethylene, carbon tetrachloride), alcohols (e.g. ethylene glycol, cellosolve), ketones (e.g. acetone, methyl ethyl ketone, cyclohexanone, isophorone), ethers (e.g. diethyl ether, dioxane, tetrahydrofuran), esters (e.g. ethyl acetate), nitriles (e.g. acetonitrile, isobutyronitrile), acid amides (e.g. dimethylformamide, dimethylacetamide), dimethyl sulfoxide, vegetable oils (e.g. soybean oil, cotton seed oil) and the like. The gaseous carrier includes for example freon gas, LPG (liquefied petroleum gas), dimethyl ether and the like. The surface active agent used for emulsification, dispersion, wetting, etc. includes for example anionic surface active agents such as the salt of alkyl sulfates, alkyl(aryl)sulfonates, dialkyl sulfosuccinates, the salt of polyoxyethylene alkylaryl ether phosphoric acid esters, naphthalenesulfonic acid/formalin condensates, etc., and nonionic surface active agents such as polyoxyethylene alkyl ether, polyoxyethylene polyoxypropylene block copolymers, sorbitan fatty acid esters, polyoxyethylene sorbitan fatty acid esters, etc. The auxiliary for formulation such as fixing agents, dispersing agents, etc. includes for example lignosulfonates, alginates, polyvinyl alcohol, gum arabic, molasses, casein, gelatin, CMC (carboxymethyl cellulose), pine oil, agar, etc. The stabilizer includes for example alkyl phosphates [e.g. PAP (isopropyl acid phosphate), TCP (tricresyl phosphate)], vegetable oils, epoxidized oils, the foregoing surface active agents, antioxidants (e.g. BHT, BHA), fatty acid salts (e.g. sodium oleate, calcium stearate), fatty acid esters (e.g. methyl oleate, methyl stearate) and the like.

The preparations thus obtained may be used as they are or in dilution with water. Also, they may be used in combination with other insecticides, acaricides, nematocides, fungicides, herbicides, plant growth regulators, fertilizers, soil improvers, feeds for animals, etc.

When the present compounds are put to practical use as an insecticidal and acaricidal composition, their dosage rate is usually from 0.1 to 100 g per 10 ares, and their application concentration is from 10 to 500 ppm when emulsifiable concentrates, wettable powders, flowable formulations, etc. are used diluted with water. Dusts, granules, oil sprays, aerosols, etc. are used as they are without dilution.

The present invention will be illustrated in more detail with reference to the following production examples, formulation examples and test examples, but it is not limited to these examples. Firstly, production examples will be given.

PRODUCTION EXAMPLE 1

Production of the Present Compound (1)

0.21 Gram of 5-chloro-2-fluoro-4-[2-chloro-4-(trifluoromethyl)phenylthio]aniline was dissolved in 6 ml of toluene, and to this solution was added dropwise a solution of 0.11 g of 2,6-difluorobenzoyl isocyanate in 4 ml of toluene with ice-cooling and stirring. After completion of addition, the reaction solution was stirred overnight at room temperature. Thereafter, 6 ml of n-hexane was added, the precipitated crystals were filtered off and dried to obtain 0.20 g of N-(2,6-difluorobenzoyl)-N'-[5-chloro-2-fluoro-4-{2-chloro-4-(trifluoromethyl)phenylthio}phenyl]urea as white crystals.

Yield 64%
m.p. 193.7° C.

PRODUCTION EXAMPLE 2

Production of the Present Compound (1)

0.32 Gram of 5-chloro-2-fluoro-4-[2-chloro-4-(trifluoromethyl)phenylthio]aniline was added to 30 ml of a 5% phosgene-toluene solution, and the mixture was heated under reflux for 3 hours. After concentrating the reaction solution, the residue obtained was dissolved in 20 ml of xylene, and 0.14 g of 2,6-difluorobenzamide was added. The solution was then stirred under reflux for 24 hours. Thereafter, the reaction solution was cooled and concentrated to obtain a crude product. This crude product was subjected to chromatography on silica gel to obtain 0.40 g of N-(2,6-difluorobenzoyl)-N'-5-chloro-2-fluoro-4-{2-chloro-4(trifluoromethyl)phenylthio}phenyl]urea as white crystals.

Yield 83%
m.p. 193°–194° C.

Some of the present compounds thus obtained will be collectively shown in Table 1.

TABLE 1

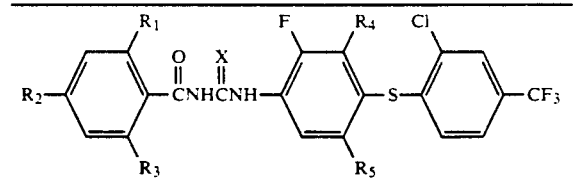

| Compound No. | $R_1$ | $R_2$ | $R_3$ | $R_4$ | $R_5$ | X | Physical constant (melting point ° C.) |
|---|---|---|---|---|---|---|---|
| (1)  | F  | H | F | H  | Cl   | O | 193.7 |
| (2)  | Cl | H | H | H  | Cl   | O | 176.1 |
| (3)  | F  | F | F | H  | Cl   | O | 195.3 |
| (4)  | F  | H | F | H  | Cl   | S | 171.0 |
| (5)  | F  | H | F | H  | F    | O | 180.9 |
| (6)  | Cl | H | H | H  | F    | O | 186.7 |
| (7)  | F  | F | F | H  | F    | O | 203.3 |
| (8)  | F  | H | F | H  | F    | S | 162.2 |
| (9)  | F  | H | F | Cl | Cl   | O | 213.0 |
| (10) | F  | H | F | H  | $CF_3$ | O | 192.8 |
| (11) | F  | H | F | H  | Br   | O | 193.2 |
| (12) | F  | H | F | H  | $CH_3$ | O | 191.9 |

PRODUCTION EXAMPLE 3

Production of an Intermediate Aniline Compound 5.00 Grams of 5-chloro-2-fluoro-4-mercaptoaniline, 12.2 g of 3,4-dichlorobenzotrifluoride and 4.31 g of potassium carbonate were dissolved in 30 ml of dimethylformamide, and the resulting solution was stirred for 2 hours at a temperature of from 100° to 110° C. in an oil bath. Thereafter, the reaction solution was poured into water and extracted with three 200-ml portions of diethyl ether. The extract obtained was washed with water, dried, filtered and concentrated. The residue obtained was subjected to chromatography on silica gel to obtain 6.57 g of 5-chloro-2-fluoro-4-[2-chloro-4-(trifluoromethyl)phenylthio]aniline.

Yield 66%
m.p. 80.8° C.
$^1$H-NMR (CDCl$_3$):
δ(ppm) 4.13(2H, br.)
6.67(1H, d, J=8.0 Hz)
6.94(1H, d, J=8.0 Hz)
7.25(1H, d, J=10.0 Hz)
7.57(1H, br. s)

PRODUCTION EXAMPLE 4

Production of an Intermediate Aniline Compound 3.00 Grams of 2,5-difluoro-4-mercaptoaniline hydrochloride, 6.60 g of 3,4-dichlorobenzotrifluoride and 4.90 g of potassium carbonate were dissolved in 30 ml of dimethylformamide, and the resulting solution was stirred for 6 hours at a temperature of from 100° to 110° C. in an oil bath. Thereafter, the reaction solution was poured into water and extracted with three 100-ml portions of diethyl ether. The extract obtained was washed with water, dried, filtered and concentrated. The residue obtained was subjected to chromatography on silica gel to obtain 3.60 g of 2,5-difluoro-4-[2-chloro-4-(trifluoromethyl)phenylthio]aniline.

Yield 69%
m.p. 95.9° C.
$^1$H-NMR (CDCl$_3$):
δ(ppm) 4.17(2H, br.)
6.62(1H, dd, J=8.0, 10.0 Hz)
6.70(1H, d, J=8.0 Hz)
7.17(1H, dd, J=6.0, 10.0 Hz)
7.56(1H, br. s)

PRODUCTION EXAMPLE 5

Production of an Intermediate Aniline Compound 1.00 Gram of 2-fluoro-5-methyl-4-mercaptoaniline hydrochloride, 2.24 g of 3,4-dichlorobenzotrifluoride and 1.59 g of potassium carbonate were dissolved in 10 ml of dimethylformamide, and the resulting solution was stirred for 6 hours at a temperature of from 110° to 120° C. in an oil bath. Thereafter, the reaction solution was poured into water and extracted with two 100-ml portions of diethyl ether. The extract obtained was washed with water, dried, filtered and concentrated. The residue obtained was subjected to chromatography on silica gel to obtain 1.27 g of 2-fluoro-5-methyl-4-[2-chloro-4-(trifluoromethyl)phenylthio]aniline.

Yield 73%
$n_D^{20.0}$ 1.592
$^1$H-NMR (CDCl$_3$):
δ(ppm) 3.95(2H, br.)
6.58(1H, d, J=8.0 Hz)
6.76(1H, d, J=9.0 Hz)
7.18(1H, d, J=11.0 Hz)
7.25(1H, dd, J=2.0, 8.0 Hz)
7.55(1H, br. s)

Some of the intermediate aniline compounds thus obtained will be shown below.

5-Bromo-2-fluoro-4-[2-chloro-4-(trifluoromethyl)phenylthio]aniline
$^1$H-NMR (CDCl$_3$):
δ(ppm) 4.08(2H, br.)
6.70(1H, d, J=8.0 Hz)
7.13(1H, d, J=8.0 Hz)
7.28(1H, d, J=10.0 Hz)
7.30(1H, dd, J=2.0, 8.0 Hz)
7.57(1H, br. s)

3,5-Dichloro-2-fluoro-4-[2-chloro-4-(trifluoromethyl)phenylthio]aniline
$^1$H-NMR (CDCl$_3$):
δ(ppm) 4.28(2H, br.)
6.65(1H, d, J=8.0 Hz)
6.98(1H, d, J=8.0 Hz)
7.35(1H, dd, J=2.0, 8.0 Hz)
7.65(1H, br. s) 2-Fluoro-5-trifluoromethyl-4-[2-chloro-4-(trifluoromethyl)phenylthio]aniline
$^1$H-NMR (CDCl$_3$):
δ(ppm) 4.21(2H, br.)
6.63(1H, d, J=8.5 Hz)
7.22(1H, d, J=7.0 Hz)
7.25(1H, d, J=10.0 Hz)
7.27(1H, dd, J=2.0, 8.5 Hz)
7.55(1H, br. s)

Formulation examples will be shown. In the examples, the present compounds are shown by Compound No. in Table 1, and parts are by weight.

FORMULATION EXAMPLE 1

Ten parts of each of the present compounds (1) to (12), 14 parts of polyoxyethylene styrylphenyl ether, 6 parts of calcium dodecylbenzenesulfonate, 35 parts of xylene and 35 parts of dimethylformamide are well mixed to obtain an emulsifiable concentrate of each compound.

FORMULATION EXAMPLE 2

Twenty parts of each of the present compounds (1) to (12), 10 parts of Fenitrothion, 3 parts of calcium lignosulfonate, 2 parts of sodium lauryl sulfate and 65 parts of synthetic hydrated silicon dioxide are well pulverized and mixed to obtain a wettable powder of each compound.

FORMULATION EXAMPLE 3

One part of each of the present compounds (1) to (12), 2 parts of Carbaryl, 87 parts of kaolin clay and 10 parts of talc are well pulverized and mixed to obtain a dust of each compound.

FORMULATION EXAMPLE 4

Twenty parts of each of the present compounds (1) to (12), 3 parts of a sodium naphthalenesulfonate/formalin condensate and 75 parts of water are well pulverized and mixed, and 2 parts of methyl cellulose is added and mixed as a thickening agent to obtain a flowable formulation of each compound.

Test examples will be shown. The present compounds are shown by Compound No. in Table 1, and compounds used as a control are shown by Compound symbol in Table 2.

TABLE 2

| Compound symbol | Structural formula | Remark |
|---|---|---|
| (A) | 2,6-difluoro-benzoyl—CNHCNH—(4-chlorophenyl) [F, F substituents on benzoyl ring; —C(O)NHC(O)NH— linker; 4-Cl on phenyl] | Diflubenzuron (compound described in US-A-3933908). |
| (B) | 2,6-dichloro-benzoyl—CNHCNH—(4-phenylthio-phenyl) [Cl, Cl on benzoyl ring; —C(O)NHC(O)NH— linker; 4-S-C₆H₅ on phenyl] | Compound described in US-A-3933908. |
| (C) | 2,6-difluoro-benzoyl—CNHCNH—(3-fluoro-4-(2-chloro-4-trifluoromethyl-phenoxy)-phenyl) | Flufenoxuron (compound described in EP-A1-161019). |
| (D) | Cl—(phenyl with 2-CH₃)—N=CH—N(CH₃)(CH₃) | Chlordimeform |

TEST EXAMPLE 1

The emulsifiable concentrates of the following test compounds obtained according to Formulation example 1 were diluted with water to a concentration of 1 ppm. Thereafter, 100 ml of each dilute solution thus obtained was put in a 180-ml polyethylene cup, and 20 last instar larvae of common mosquito (*Culex pipiens pallens*) were liberated therein. The larvae were bred on a bait until emergence to obtain an emergency inhibitory ratio (two replications).

The results are shown in Table 3.

TABLE 3

| Test compound | Emergence inhibitory ratio (%)* |
|---|---|
| (1) | A |
| (2) | A |
| (3) | A |
| (4) | A |
| (5) | A |
| (6) | A |
| (7) | A |
| (8) | A |
| (9) | A |
| (10) | A |
| (11) | A |
| (12) | A |
| No treatment | C |

*Emergence inhibitory ratio (%):
A: More than 90%
B: From 80 to 90%
C: Less than 80%

TEST EXAMPLE 2

The emulsifiable concentrates of the following test compounds obtained according to Formulation example 1 were diluted with water to a concentration of 15 ppm. Two milliliters of each dilute solution thus obtained was applied onto 13 g of artificial diet for tabacco cutworm (*Spodoptera litura*) which were then put in a polyethylene cup of 11 cm in diameter. Then, ten fourth instar larvae of tabacco cutworm were liberated in the cup. After six days, the dead and alive were examined to obtain mortality (two replications).

The results are shown in Table 4.

TABLE 4

| Test compound | Mortality (%) |
|---|---|
| (1) | 100 |
| (2) | 100 |
| (3) | 100 |
| (4) | 100 |
| (5) | 100 |
| (6) | 100 |
| (7) | 100 |
| (8) | 100 |
| (10) | 100 |
| (11) | 100 |
| (12) | 100 |
| No treatment | 5 |

TEST EXAMPLE 3

The emulsifiable concentrates of the following test compounds obtained according to Formulation example 1 were each diluted with water to a concentration of 100 ppm to obtain a dilute solution. From 20 to 60 deutonymphs of carmine spider mite (*Tetranychus cinnabarinus*) were transferred onto leaves in a petri dish, and 3 ml of the dilute solution was sprayed thereon. After three days, the number of adults was counted to obtain an adult emergence inhibitory ratio.

The results are shown in Table 5.

TEST EXAMPLE 4

The emulsifiable concentrates of the following test compounds obtained according to Formulation example 1 were each diluted with water to a concentration of 100 ppm to obtain a dilute solution. Thirty female adults of carmine spider mite (*Tetranychus cinnabarinus*) were transferred onto a leaf in a petri dish, and 3 ml of the dilute solution was sprayed thereon. After air-drying, 18 female adults were transferred onto untreated leaves in a petri dish, and allowed to oviposit for three days. The eggs obtained were stored in a chamber controlled at 27° C. in an artificial weather room. After six days, hatchability of the eggs was examined to obtain a sterilization ratio.

The results are shown in Table 5.

TABLE 5

| Test compound | Adult emergence inhibitory ratio (%)* | Sterilization ratio (%)** |
| --- | --- | --- |
| (1) | 100 | 95 |
| (2) | 100 | — |
| (3) | 100 | — |
| (4) | 100 | — |
| (5) | 100 | 99 |
| (6) | 100 | 96 |
| (7) | 100 | 99 |
| (8) | 100 | 95 |
| (9) | 97 | — |
| (10) | 98 | 72 |
| (11) | 100 | — |
| (12) | 100 | — |
| (A) | 5 | 0 |
| (B) | 2 | 0 |
| (C) | 60 | 0 |

*Adult emergence inhibitory ratio (%) = $\left(1 - \dfrac{\text{adult emergence ratio in the plot treated with chemicals}}{\text{adult emergence ratio in the plot treated with water}}\right) \cdot 100$

**Sterilization ratio (%) = $\left(1 - \dfrac{\text{hatchability in the plot treated with chemicals}}{\text{hatchability in the plot treated with water}}\right) \cdot 100$

TEST EXAMPLE 5

The emulsifiable concentrates of the following test compounds obtained according to Formulation example 1 were each diluted with water to a concentration of 100 ppm to obtain a dilute solution. The female adults of carmine spider mite (*Tetranychus cinnabarinus*) were transferred onto leaves and allowed to oviposit for 24 hours. The eggs obtained were dipped for 5 seconds in the dilute solution. After treatment, the eggs were stored in a chamber controlled at 27° C. in an artificial weather room. After six days, the number of unhatched eggs was examined to obtain an ovicidal ratio.

The results are shown in Table 6.

TABLE 6

| Test compound | Ovicidal ratio (%) |
| --- | --- |
| (1) | 100 |
| (5) | 98 |
| (10) | 95 |
| (11) | 100 |
| (12) | 100 |
| (A) | 5 |
| (B) | 3 |

TABLE 6-continued

| Test compound | Ovicidal ratio (%) |
| --- | --- |
| (C) | 10 |

TEST EXAMPLE 6

Ten female adults of carmine spider mite (*Tetranychus cinnabarinus*) were transferred onto each leaf of potted kidney bean in a primary leaf stage, which had elapsed seven days after sowing, and stored in a constant-temperature room kept at 25° C. After six days, the emulsifiable concentrate of the following test compounds obtained according to Formulation example 1 was diluted with water so that the active ingredient concentration was 500 ppm. Ten ml of the dilute solution was sprayed onto the plant on a turn table by a spray gun, and 2 ml of the diluted solution was treated on the pot soil. After 20 days, the degree of damage of each kidney bean by spider mites was examined.

The degree of damage was classified into three stages, —, + and + +.

—: Little damage is observed.
+: Slight damage is observed.
+ +: Same damage as in the untreated plot is observed.

The results are shown in Table 7.

TABLE 7

| Test compound | Degree of damage |
| --- | --- |
| (1) | — |
| (2) | — to + |
| (3) | — |
| (4) | — to + |
| (5) | — |
| (8) | — |
| (10) | — to + |
| (11) | — to + |
| (12) | — |
| (D) | + + |
| No treatment | — + |

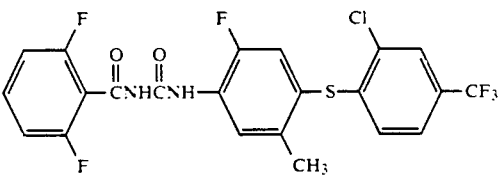

What is claimed is:

1. A benzoylurea derivative represented by the formula:

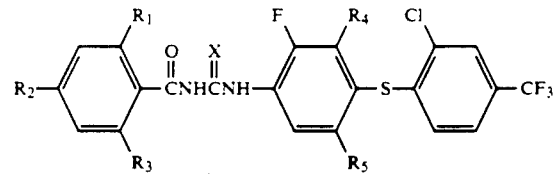

wherein $R_1$ is chlorine or fluorine, each of $R_2$ and $R_3$, which may be the same or different, is fluorine or hydrogen, $R_4$ is hydrogen, $R_5$ is halogen, methyl or trifluoromethyl, and X is oxygen or sulfur.

2. The benzoylurea derivative according to claim 1, wherein $R_1$ is a chlorine or fluorine atom, $R_2$ is a hydrogen atom, $R_3$ is a hydrogen atom when $R_1$ is a chlorine atom, and a fluorine atom when $R_1$ is a fluorine atom, $R_4$ is a hydrogen atom, $R_5$ is a fluorine, bromine or chlorine atom or a methyl or trifluoromethyl group, and X is an oxygen atom.

3. The benzoylurea derivative according to claim 1 or 2 represented by the formula, 4. The benzoylurea derivative according to claim 1 or 2 represented by the formula,

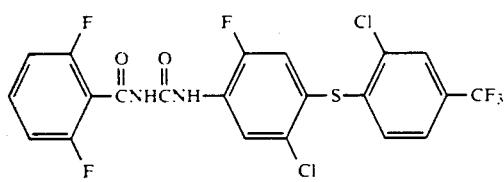

5. The benzoylurea derivative according to claim 1 or 2 represented by the formula.

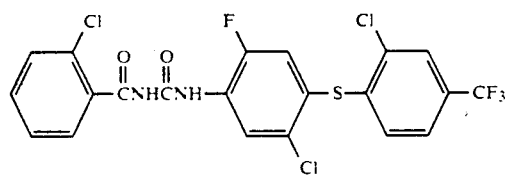

6. The benzoylurea derivative according to claim 1 or 2 represented by the formula.

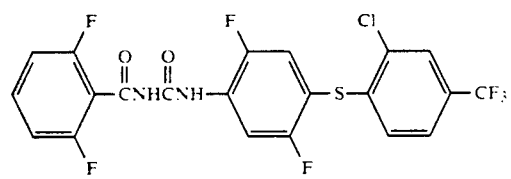

7. The benzoylurea derivative according to claim 1 or 2 represented by the formula,

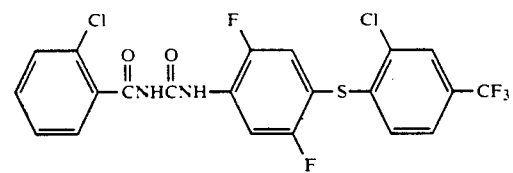

8. The benzoylurea derivative according to claim 1 or 2 represented by the formula,

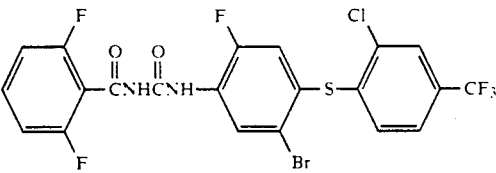

9. An acaricidal composition which comprises as an active ingredient an acaricidally effective amount of a benzoylurea derivative according to claim 1, and an inert carrier or diluent.

10. The acaricidal composition according to claim 9, wherein the benzoylurea derivative is a compound wherein $R_1$ is a chlorine or fluorine atom, $R_2$ is a hydrogen atom, $R_3$ is a hydrogen atom when $R_1$ is a chlorine atom, and a fluorine atom when $R_1$ is a fluorine atom, $R_4$ is a hydrogen atom, $R_5$ is a fluorine, bromine or chlorine atom or a methyl or trifluoromethyl group, and X is an oxygen atom.

11. A method for controlling or exterminating acarids which comprises applying as an active ingredient an acaricidally effective amount of the benzoylurea derivative according to claim 1 to the locus where acarids propagate.

12. A composition for inhibiting the adult emergence of acarids which comprises an acaricidally effective amount of a benzoylurea derivative according to claim 1 as an active ingredient and an inert carrier.

13. A method for inhibiting the adult emergence of acarids which comprises applying an acaricidally effective amount of a benzoylurea derivative according to claim 1 to the locus where acarids propagate.

14. A composition for sterilizing the female adults of and acarids which comprises a sterilizing effective amount of a benzoylurea derivative according to claim 1 as an active ingredient and an inert carrier.

15. A method for sterilizing the female adults of acarids which comprises applying a sterilizing effective amount of a benzoylurea derivative according to claim 1 to the locus where the acarids propagate.

16. A method for controlling eggs of acarids which comprises applying an ovicidally effective amount of a benzoylurea derivative according to claim 1 to the locus where acarids propagate.

* * * * *